US008206675B2

(12) United States Patent
Thierauf

(10) Patent No.: US 8,206,675 B2
(45) Date of Patent: Jun. 26, 2012

(54) NONTOXIC POLYETHOXYSILOXANE MATERIAL OR THE PRODUCTION OF BIOLOGICALLY RESORBABLE AND/OR BIOACTIVE ARTICLES CONTAINING POLYETHOXYSILOXANE MATERIAL, THE PRODUCTION THEREOF, AND THE USE THEREOF

(75) Inventor: Axel Thierauf, Neufahrn i. NB. (DE)

(73) Assignee: Bayer Innovation GmbH, Duesseldorf (DE)

( * ) Notice: Subject to any disclaimer, the term of this patent is extended or adjusted under 35 U.S.C. 154(b) by 182 days.

(21) Appl. No.: 12/602,773

(22) PCT Filed: Jun. 3, 2008

(86) PCT No.: PCT/DE2008/075002
§ 371 (c)(1),
(2), (4) Date: Dec. 3, 2009

(87) PCT Pub. No.: WO2008/148384
PCT Pub. Date: Dec. 11, 2008

(65) Prior Publication Data
US 2010/0174045 A1      Jul. 8, 2010

(30) Foreign Application Priority Data
Jun. 4, 2007  (DE) .......................... 10 2007 026 043

(51) Int. Cl.
*C01B 15/14*  (2006.01)
(52) U.S. Cl. .......................................... 423/325
(58) Field of Classification Search ............ 528/10; 423/325
See application file for complete search history.

(56) References Cited

U.S. PATENT DOCUMENTS 6,764,690 B2 * 7/2004 Ahola et al. ................. 424/422
7,727,543 B2 * 6/2010 Koskinen et al. ............ 424/426

FOREIGN PATENT DOCUMENTS

| DE | 196 09 551 C1 | 7/1997 |
| DE | 10 2004 063 599 A1 | 7/2006 |
| WO | WO 2006/069567 A | 7/2006 |

OTHER PUBLICATIONS

Sakka, Sol-Gel Technology for Thin Films, Fibers, Preforms, Electronics and Speciality Shapes, ed. L.C. Klein, Park Ridge, NY, 1988, p. 140 and figure 2.7.
"Silsesquioxanes, Bridging the Gap Between Polymers and Ceramics", Chemfiles, vol. 1, No. 6, 2001 (Aldrich Chemical).
www.photolagen.com, last accessed Mar. 12, 2010.

* cited by examiner

*Primary Examiner* — Margaret Moore
(74) *Attorney, Agent, or Firm* — Norris McLaughlin & Marcus PA

(57) ABSTRACT

The present invention relates to a polyethoxysiloxane (PES) material to be obtained in that (a) a first hydrolysis condensation reaction of a maximum of one group X of one or more different Si compounds of the formula (I) SiX4 (I) in which the groups X are the same or different and represent hydroxy, hydrogen, or ethoxy (EtO), are catalyzed in an acidic fashion at an initial pH value of 0 to $\leq 7$, is conducted in the presence of ethanol (EtOH) or an ethanol-water mixture as a solvent over a time period of 1 to 24 hours at a temperature of 0° C. to 78° C, (b) a second hydrolysis condensation reaction of the material obtained in step (a) is conducted while simultaneously removing the solvent by successive evaporation in a gas diffusion-tight container at a pressure of 100 to 1013 mbar, preferably at a slight negative pressure of 300 mbar to 800 mbar and a temperature of 50-78° C. until a drastic increase in viscosity (at a shear rate of 10 s$^{-1}$ at 4° C.) to 0.5 to 2 Pa·s until a constant weight is attained and a cyclotetrasiloxane of the general formula $((SiO(OH)_{0.75}(OEt)_{1.25} \times \frac{1}{64} H_2O)_4$ and a molar mass of 4*approx. 114 g=approx. 456 g; (c) said PES material is cooled in a closed container over a time period from a few minutes to a few hours, and (d) the PES material obtained from step (c) is converted into an rPES material by a third hydrolysis condensation reaction.

13 Claims, No Drawings

US 8,206,675 B2

NONTOXIC POLYETHOXYSILOXANE MATERIAL OR THE PRODUCTION OF BIOLOGICALLY RESORBABLE AND/OR BIOACTIVE ARTICLES CONTAINING POLYETHOXYSILOXANE MATERIAL, THE PRODUCTION THEREOF, AND THE USE THEREOF

CROSS-REFERENCE TO RELATED APPLICATIONS

The present application is a National Phase Application of International Application No. PCT/DE2008/075002, filed Jun. 3, 2008, which claims priority to German Patent Application No. 10 2007 026 043.3, filed Jun. 4, 2007, which applications are incorporated herein fully by this reference.

This invention relates to a nontoxic polyethoxysiloxane material (PES material), optionally a ripened poly-ethoxysiloxane material (rPES material) which is preferably formed as one of multiple different polyethoxysiloxane materials (PES materials). Such an rPES material (r stands for ripe, ripened) is, in accordance with the present invention, spinnable into bioabsorbable and/or bioactive fibers as one of the PES materials and then further processible into fibrous nonwoven webs as other PES materials, for example. The present invention further relates to processes for producing the ripened or unripened PES material, for producing the bioabsorbable and/or bioactive PES materials, and to uses for these materials.

There are many different endeavors underway to develop bioabsorbable materials for various applications in human medicine and medical engineering, but also in other technical fields such as filter technology, biotechnology or the insulant industry. These sectors, moreover, have higher and higher requirements, particularly with regard to the bioactivity and toxicological properties of the materials.

Absorbable silicon polymers are known in the prior art. DE 196 09 551 C1 describes biodegradable and -absorbable fibrous structures. These fibers are obtainable in a sol-gel process by drawing fibers from a spinning dope and drying them, if desired. The spinning dope contains one or more partially or completely hydrolytically condensed compounds of silicon, which are derived from monomers of the general formula $SiX_4$ by hydrolytic condensation. The fibers have the disadvantage that degraded as-spun they do not show good results in cytotoxicity tests and in some instances even have to be categorized as cytotoxic. Cytotoxicity is absolutely unacceptable for use in human medicine, medical engineering, filter technology, biotechnology or the insulant industry, particularly in the field of wound healing or the filtration of cells from bodily fluids.

The process for producing the fibers according to DE 196 09 551 C1, furthermore, has the disadvantage that the resulting mixture following removal of the solvent in the hydrolysis-condensation step is a multiphase mixture and has to be subjected to filtration to remove the solid material formed. Other liquid silicon polymers, which may be toxic, cannot be removed at all by filtration. In addition, a large proportion of the spinnable sol is lost, inter alia due to the formation of the solid phase and due to the mandatory filtering step. The process of DE 196 09 551 C1 also allows the formation, during ripening, of a considerable proportion of a gellike phase of comparatively highly condensed silicon compounds. This further reduces the proportion of spinnable sol dope.

It is an object of the present invention to provide a nontoxic bioabsorbable and/or bioactive material, materials containing this material and a process for producing such a nontoxic material.

Bioactivity herein is to be understood as meaning a positive interaction between material(s) on the one hand and tissue (wound tissue, for example) on the other with subsequent differentiation of the tissue and, as a consequence thereof, binding or adhesion of tissue along the interface between material(s) and (recipient) tissue.

I have found that this object is achieved by a sol, or microemulsion (colloidal solution), as set forth in claim 1, which microemulsion is herein also referred to as PES material. Such a microemulsion/colloidal solution is obtainable by (a) performing a first hydrolysis-condensation reaction (HCR) of at most one X radical of one or more different silicon compounds of formula I

$$SiX_4 \qquad (I),$$

where the X radicals are the same or different and each represent hydroxyl, hydrogen or ethoxy (EtO), acid catalyzed at an initial pH of 0 to $\leq 7$, in the presence of ethanol (EtOH) or of an ethanol-water mixture as solvent, for a period of 1 to 24 h at a temperature of 0° C. to 78° C. (boiling point of ethanol), (b) performing a second HCR of the material obtained in step (a) while at the same time removing the solvent by gradual evaporation in a closed, gas diffusion tight container (rotary evaporator) at a defined pressure, preferably at a slight underpressure of about 500 mbar, a temperature of preferably 50-78° C., more preferably about 70° C., until a drastic increase in viscosity to about 1 Pa·s, until constant weight and until formation of a cyclotetrasiloxane of molar mass 4×about 114=about 456 g, of the general formula $((SiO(OH)_{0.75}(OEt)_{1.25} \times \frac{1}{64} H_2O)_4$;

(c) cooling this PES material in a closed, preferably gas diffusion tight container rapidly over a period of a few minutes to a few hours, preferably within half an hour, and (d) converting the PES material obtained from (c) into an rPES material via a third HCR.

It is to be noted that the nontoxic, bioabsorbable and/or bioactive PES or rPES material of the present invention is obtainable without its method of making comprising, or having to comprise, one or more filtration steps. This is a significant difference to the process known from DE 196 09 551 C1.

If desired, step (d) is followed by a fourth HCR as one of the following steps (e1) to (e4), whereby the rPES material obtained in step (d) can be used to produce one of the PES materials such as fiber (e1), powder (e2), monolith (e3) or coating (e4). Accordingly, these steps involve the following measures:

(e1) spinning the rPES material into bioabsorbable and/or bioactive fibers;

(e2) processing the material from step (d) into a powder by subjecting the rPES material obtained to a drying operation, more particularly a lyophilization, and comminuting (grinding) the dried PES material to a powder;

(e3) pouring the rPES material from step (d) into a mold and drying;

(e4) applying the rPES material from step (d) to an article to be coated, or dipping the latter into the rPES material.

It is particularly preferable when the rPES material(s) have a pH of 5 to 7, particularly 6, in use in order that it/they may have an acceptable (physiological) tolerability. Below pH 5, the material is intolerable if only because of its acidic nature.

Since step (b) involves evaporating to constant weight, i.e., until no or almost no water is left, acid strength in the water-free system cannot be defined as a specific pH. Rather, the optional buffering (i.e., addition of a suitable buffer or or an alkali) or reduction in acid strength (by expelling/evaporating $NO_2$ in the case of nitric acid, for example) in (b) should be effected such that the rPES material ultimately obtained after (e), or the PES materials molded therefrom, have a pH of 5 to 7, particularly of $\geqq 6$, at watering.

To achieve this, it is preferred to reduce the acid strength, or buffer the effect of the acid, in step (b). If this is not done in step (b) or not done to the preferred level, it can also be carried out thereafter in step (c) or (e) or else only directly before application of the PES materials (to the skin/wound for example). However, setting the correct acid strength or effect in step (b) is unequivocally preferred according to the present invention.

Reducing the acid effect in one of the steps (b), (c) or (e) or during the watering of the PES materials can be effected particularly by means of Tris (tris(hydroxymethyl)aminomethane) in the form of the free base or of a salt (e.g. Tris acetate, Tris phosphate).

The individual steps of the above reactions will now be more particularly discussed.

Step (a)

In accordance with what is preferable according to the present invention, tetraethoxysilane (TEOS) is used as sole silicon compound of formula I in the (first) HCR of the present invention.

The initial pH of 0 to $\leqq 7$, preferably of 2-3.5, is set with dilute nitric acid (for example with 1N, preferably with 0.01N $HNO_3$) for example. But in principle it is possible to use any acidic mixtures or solutions suitable for producing NO or $NO_2$ in situ. These can also be, for example, acidic mixtures and solutions which in a physiological environment with molecular oxygen produce nitrogen monoxide (NO) enzymatically (by means of a nitroxide synthase, NOS), which in turn is rapidly converted by the body to $NO_2$, or can also be organic nitrates or nitrate esters (so-called NO donors), for example ethyl nitrate, which form NO with the aid of an organic nitrate reductase. Thiol groups (cysteine) are needed for this enzymatic release of NO.

In addition to dilute nitric acid, therefore, preference according to the present invention is also given to an aqueous or alcoholic (more preferably: an aqueously diluted ethanolic) solution of a physiologically tolerable acid (for example citric acid, succinic acid, tartaric acid, acetic acid or ascorbic acid) and of at least one essential amino acid (for example L-arginine, more preferably: L-valine, L-leucine, L-isoleucine, L-phenylalanine, L-thyroxine, L-methionine, L-lycine or L-tryptophan) or of a nonessential amino acid (for example, L-glutamine, L-glutamic acid, L-asparagine, L-aspartic acid, L-cysteine, L-glycine, L-alanine, L-proline, L-histidine, L-tyrosine) as substrate of the NOS to set the pH to the desired value in the weak to medium acidic range.

When the pH is set using dilute nitric acid (for example 0.01N), this is preferably used in a molar ratio of silicon compound(s) of formula (I)/nitric acid in the range from 110:1 to 90:1 and more preferably 100:1. The nitric acid is advantageously used such that the molar ratio of silicon compound of formula I (for example TEOS)/$HNO_3$ is about 100:1.

The solvent which according to the present invention is preferably used in step (a) is an ethanol-water mixture, which has the function of dissolving, or at least emulsifying, the silicon compound(s) of formula I. When the silicon compound of formula I is TEOS, water does not dissolve/emulsify the silicon compound of formula I and therefore it is preferable to admix with EtOH as solubilizer. The preferred amount of EtOH is in the range from 1 to 1.5 mol/mol of TEOS and, in a particularly preferred embodiment, is 1.26 mol/mol of TEOS.

A very particularly preferred reaction batch is carried out as follows according to the present invention. The reaction vessel is initially charged with 1 mol of TEOS, to which 1.26 mol of EtOH are then added. This mixture is stirred, so that the EtOH dissolves the TEOS. Separately, 27.81 g of 1N $HNO_3$ (corresponds to 1.75 g of $HNO_3$) are diluted with 60.38 g of $H_2O$ (the total mass of dilute nitric acid is thus 88.19 g, of which 86.44 g are accounted for by $H_2O$, corresponding to 4.8 mol, and 1.75 g by $HNO_3$, corresponding to 0.028 mol; the $H_2O/HNO_3$ molar ratio is 4.8/0.028=172). Then, 33.07 g of the dilute nitric acid are added to the ethanolic TEOS solution (so that 1.8 mol of $H_2O$ and 0.01 mol of $HNO_3$ are used per 1 mol of TEOS).

The first HCR proceeds exothermically. The first HCR means according to the present invention, as illustrated using TEOS as an example, that one EtO group in a TEOS molecule hydrolyzes and the resulting OH group condenses by dimerization and water elimination with continuous stirring. In other words, the two solutions (for example TEOS in EtOH and dilute nitric acid) are combined at room temperature (RT), while the temperature during the reaction of $2\,SiX_4$ (i.e., of 2 TEOS for example) via hydrolysis and condensation of one EtO radical at a time to form $X_3Si$—O—$SiX_3$ (for example $(EtO)_3$—Si—O—Si—$(EtO)_3$) rises to about 50-60° C. The initial temperature in the case of the first HCR is not significant (since the reaction anyhow proceeds exothermically). The temperature can be RT, but it can also be below or above the particular RT, for example 5, 10, 15, 20, 35, 45, 60 or 70° C. The temperature merely has to be sufficiently high so that the first HCR may proceed.

It is particularly preferable according to the present invention to avoid the hydrolysis of more than one EtO group per TEOS molecule. RT (about 20° C. or, where appropriate, 18-25° C.) is therefore preferable for economic and practical reasons. Higher temperatures up to 78° C. are likewise suitable as long as they are in the range from 0° C. to 78° C., preferably in the range from 10° C. to 70° C. or in the range from 20° C. to 60° C. It will be appreciated that the temperature is subject to the customary relationship in chemistry whereby a lower temperature requires longer reaction times, and vice versa. In a preferred embodiment of the present invention, this first HCR is performed over a period of 1-12 hours. Periods of 5-8 h are particularly preferred.

The sol cools down to RT during the stirring. Once the sol has reached RT and the stirring has been terminated, step (b) must follow without delay. The reaction mixture shall accordingly not stand unnecessarily at RT without stirring without (b) being performed. Otherwise, the HCR will continue and the mixture will form gellike, more highly condensed silicon compounds.

The first HCR is preferably performed batchwise in a stirred container. The silicon compound of formula I (for example TEOS) and the solvent (for example ethanol) are preferably charged as initial charge. This is followed by the expeditious addition of the acid, preferably in the form of 0.01N $HNO_3$ (for example 0.01 mol of $HNO_3$ per mole of TEOS). Owing to the acid strength in the reaction mixture, the first HCR proceeds rapidly, and the contents of the container will heat up to 50° C. to 60° C. before the temperature starts to sink (as a consequence of natural cooling to the ambient temperature, i.e. without external cooling) during the reaction time (i.e., in step (a)).

Step (b)

In a second HCR of the material obtained in step (a), in a closed, gas diffusion tight container (rotary evaporator) with simultaneous removal of the solvent (water, ethanol) by gradual evaporation at a pressure of 100 to 1013 mbar, preferably at 500 to 800 mbar, a reaction temperature of RT to 70° C., preferably 60-70° C. and preferably while slowly rotating at 20 rpm, cyclotetrasiloxane of the general formula: $((SiO(OH)_{0.75}(OEt)_{1.25} \times \frac{1}{64} H_2O)_4$ with a molar mass of 4×about 114 g=about 456 g is formed accompanied by a drastic increase in viscosity.

Step (b) should absolutely take place in the absence of water in order that no further hydrolysis can take place. Absence of water in this context is to be understood as meaning that no further water is added from the outside or gets into the reaction mixture via atmospheric humidity; however, owing to the condensation reaction, in the course of which water is formed, and any water added as solvent in step (a), the reaction mixture in step (b) is not water-free.

The evaporation temperature should not exceed 78° C. (boiling point of EtOH) since the solvent (mixture) will otherwise form bubbles. Temperatures above 60° C. are particularly preferable since at lower temperatures the acid, the $NO_2$ in the case of $HNO_3$, can no longer evaporate to a sufficient degree and the remaining HCR would proceed significantly more acidically and ultimately a higher acid concentration would remain in the material.

In accordance with this recognition on the part of the inventors, it is particularly preferable to allow step (b), the step of the so-called reactive evaporation, to proceed until the viscosity has risen abruptly to about 1 Pa·s and constant weight is reached, alternatively until a cyclotetrasiloxane is present, preferably with simultaneous, ideally substantial reduction in acid strength (by evaporating the nitric acid or to be more precise the $NO_2$). A person skilled in the art will recognize the end of step (b) from the viscosity, which starts to rise substantially and reaches values of 0.5-2 Pa·s.

It is preferable to end (b) by cooling to temperatures below 10° C., see under step (c), when the viscosity of the reaction mixture is about 1 Pa·s. At this stage, a one-phase, "warm" microemulsion or to be more precise a one-phase, "warm" sol having a viscosity of 0.5 to 2 Pa·s at a shear rate of $10 s^{-1}$ at 4° C. (PES material) will be present.

The reactive evaporation is carried out at temperatures which permit the removal of water, EtOH and, as the case may be, $NO_2$ in the case of using nitric acid. 70° C. is preferable from a practical point of view, but slightly lower temperatures such as 50° C. or 60° C. are also preferable. Without the inventors feeling themselves tied to their theoretical consideration, supported by initial experimental data, they do postulate for the PES material obtained in step (b) ("warm" microemulsion or "warm" sol) a composition of $((SiO(OH)_{0.75}(OC_2H_5)_{1.25} \times \frac{1}{64} H_2O)_4$ (MW=4×113.28 g=453.12 g) in the form of quadruple formations which are four Si—O units, i.e., constitute eight-membered rings.

The attentive reader can't have failed to recognize that step (b) involves the intermediates obtained in (a) undergoing further reaction by eliminating EtOH or water followed by removal thereof. When step (b) is not performed in a closed vessel or is not carried on to weight constancy or to an increased viscosity (preferably to 1 Pa·s), physiologically undesirable substances will remain behind in the PES material, which are difficult to remove, if at all, during the steps (c), (d) and/or (e1)-(e4).

When step (a) utilizes dilute nitric acid, the possible and preferred reduction in acid strength in step (b) is effected by the acid decomposing during the reactive evaporation to form $NO_2$, $O_2$ and water. $NO_2$ (boiling point ~21.2° C.), however, is then only expelled to a very substantial degree in that a very small portion remains enclosed in the microemulsion/sol. When, however, the system utilizes an organic acid/arginine in place of nitric acid, the pH is raised, or the acid strength reduced, if desired, by means of, for example, Tris solutions (when the acid, and acetic acid as an example, cannot be expelled).

It has now been ascertained that, surprisingly, observing the conditions as described above for steps (a) and (b) and removing the solvent in step (b) provides a microemulsion which no longer requires any filtration, i.e., is single phase, before the ripening in step (d).

Step (c)

This step, which is a cooling operation, is sensibly characterized in that the "warm" microemulsion obtained in step (b) is transferred expeditiously, i.e., within a few minutes to a few hours, preferably within half an hour, into a closed, preferably gas diffusion tight, container and cooled down to the temperature at which step (d) is performed.

Accordingly, the temperatures which represent the end point of the cooling operation are preferably in the range from −20° C. to 10° C., preferably in the range from 2° C. to 4° C. and more preferably equal to 4° C. The ingress of moisture, for example as atmospheric humidity or moisture adhering to the container, must absolutely be avoided. Where appropriate, this step also involves an adjustment being made to the material such that the pH of the later materials to be applied to the body is pH 5 to 7, preferably pH>6.

Step (d)

The kinetic controlled ripening is a constituent part of the process of the present invention in that without it the reaction mixture (PES material) obtained after step (c) would not be processible, for example spinnable or else coatable, at all. This step (d) features a third HCR wherein the viscosity of the reaction mixture increases as a result of the quadruple formations (cyclotetrasiloxanes) generated in step (b) coming together to form cubes or cages (silasesquioxanes) of the general formula $Si_8O_{12}(OH)_2(EtO)_6$ having eight silicon atoms at the corners and twelve oxygen bridges at the edges. Depending on the viscosity to be obtained, the silasesquioxanes thus form chains of cubes/cages, or oligosilasesquioxanes.

Step (d) is effected according to the present invention in closed preferably gas diffusion tight vessels, for example in so-called ripening beakers, preferably in the vessels already used for step (c). The ingress of moisture or of other gases, including $CO_2$, must be absolutely avoided. The preferred way of performing step (d) in the present invention is at a temperature of (above) −20° C. to 10° C. over a period of 1 day up to 4 weeks, preferably at 2° C. to 4° C. and over a period of 3 to 18 days. It is particularly preferable to perform the ripening over a period of 3 to 5 days at 4° C., in particular by vibration-free storage of the reaction mixture in closed, preferably gas diffusion tight vessels. However, ripening can with similar preference be effected at any temperature in the range from (above) −20° C. to 10° C.

A person skilled in the art will recognize that temperature and reaction time are two mutually dependent variables which are adapted to each other, preferably such that the material obtained in step (c) has fully converted to a silasesquioxane of the general formula $Si_8O_{12}(OH)_2(EtO)_6$ and the rPES material thus obtained in (d) assumes a dynamic viscosity which qualifies and prepares it for the performance of one of the steps (e1) to (e4). When the material is to be spun into fiber in a step (e1), the dynamic viscosity at the end of (d) should be about 30 to 55 Pa·s (shear rate $10 s^{-1}$ at 4° C.) with a loss factor of 3.5 (the loss factor is the quotient formed from the elastic and inelastic contributions to dynamic viscosity). When, by contrast, the material is to be processed in a step (e2) to form a powder, the dynamic viscosity at the end of (d) is about 60 Pa·s (shear rate 10 s$^{-1}$ at 4° C.). In the case of the material being processed into a monolith (in a step (e3)), the dynamic viscosity at the end of (d) is preferably not less than 70 Pa·s (shear rate 10 s$^{-1}$ at 4° C.). And when the material is to be used in a step (e4) for coating articles or surfaces, the dynamic viscosity is less than or equal to 10 Pa·s (shear rate 10 s$^{-1}$ at 4° C.), depending on the layer thickness desired.

The low temperature during the ripening in the ripening beaker is the reason why, starting from the quadruple formation (cyclotetrasiloxane), a kinetically controlled hydrolysis and condensation (the third HCR) takes place, so that silasesquioxanes of the general form: $Si_8O_{12}(OH)_2(EtO)_6$ are formed. These silasesquioxanes aggregate via hydrogen bonding.

Without the inventors feeling themselves tied to their theoretical consideration, supported by initial experimental data, they do postulate a composition of the following kind for the rPES material obtained in step (d): during aggregation, the third HCR continues, so that the silasesquioxanes (cubes) come together to form oligosilasesquioxanes (chains of cubes) of the general formula $[OSi_8O_{12}(OH)_2(EtO)_5]$ and lead to a preferably one-dimensional formation of chains. These chains of cubes form linear (quasi one-dimensional) oligomeric structures which can easily reach a length of 100-1000 nm. The chains of cubes are each aggregated together via hydrogen bonds and still contain residual ethoxy groups.

Macroscopically, a one-dimensional chained structure manifests itself in a particular form of viscosity, the so-called structural viscosity. Increasing HCR of the cubes to form chains of cubes continues to increase the viscosity. The formation of chains of cubes is carried out until the desired viscosity is present.

The end product of ripening in the ripening beaker is accordingly an infinitely durable sol (the rPES material) having a certain structural viscosity. Structural viscosity is the property of a fluid of responding to high shearing forces by exhibiting a lower viscosity; the greater the rate of shear acting on the fluid, the less viscous the fluid is. The viscosity decreases as a result of the action of a force on the oligomers in the sol, the action of a force ensuring that the individual sol particles (oligosilasesquioxanes in this instance) become aligned and therefore are better able to glide past each other; for further information on this subject, particularly concerning the size and shape of the structures which make up spinnability, see Sakka in *Sol-Gel Technology for Thin Films, Fibers, Preforms, Electronics and Specialty Shapes*, ed. L. C. Klein, Ncyes, Park Ridge, N.Y., 1988, page 140 and FIG. 2.7).

Advantageously, the present invention thus (very substantially) suppresses the competing formation of a three-dimensional polymeric gel network, the end product of the process according to the present invention, after step (d), thus advantageously being a hydrophobic ethoxy-containing single-phase sol of oligosilasesquioxanes (chains of cubes) without gel content, said sol being (very substantially) free of water and being most suitable for permanent storage, transportation and distribution.

Since the kinetically controlled ripening, i.e., step (d), proceeds only minimally, if at all, at below −20° C., the PES material can be "frozen" at −20° C. after step (c) because it has likewise infinite durability at that temperature. This is a preferred variant in that the PES material (before step (d)) can be stored and transported exactly like the rPES material after step (d).

Without the inventors once more feeling themselves tied to their theoretical consideration and preliminary experimental data, they do postulate for the rPES material obtained in step (d) a silasesquioxane of the general formula $Si_8O_{12}(OH)_2(EtO)_6$ or an oligosilasesquioxane of the composition $[OSi_8O_{12}(OH)_2(EtO)_5]$.

Silasesquioxanes are named for the 1.5-fold or sesquistoichiometric oxygen per silicon atom. This type of compound is known to exist in a number of geometric structures, including ladder, cube or cage structures. A fully condensed silasesquioxane has the structure $[RSiO_{1.5}]_n$ and is referred to as polyhedral oligomeric silasesquioxane (POSS). Fully through-condensed POSSs are known from the literature and are commercially available (for example from Sigma-Aldrich, St. Louis, MO, USA) with a large number of substituents. Sigma-Aldrich offers for example an octamethyl-POSS of the formula $(CH_3)_8Si_8O_{12}$ and also a cyclopentyl-POSS-silanol of the formula $(C_5H_9)_7Si_8O_{12}(OH)$, which are both sufficiently different from the oligosilasesquioxane $[OSi_8O_{12}(OH)_2(EtO)_5]$ of the present invention. Nor is such a pentaethoxy-POSS-silanol known in the literature.

Also known are silasesquioxanes of the empirical formula $RSiO_{1.5}$, where the R substituents can theoretically be the following groups: hydrogen, hydroxyl, alkyl, alkenyl, alkoxy and aryl. Silasesquioxanes known in the literature include those having the following R substituents: methyl, propyl, allyl, methacryloyl, phenyl, hydrogen, hydroxyl.

Step (e1)

The spinning operation for processing the sol into fiber is carried out under customary conditions as described for example in DE 196 09 551 C1 and DE 10 2004 063 599 A1. The dynamic viscosity of the sol is preferably in the range from 30 to 55 Pa·s (shear rate 10 s$^{-1}$ at 4° C.), and the loss factor is 3.5. In the spinning operation, the rPES is blown via a pressurized vessel through a die head having up to 100 individual dies (pressure in container 1-100 bar, advantageously 20 bar). The ultimately resulting fiber consists in general of chains of cubes (oligosilasesquioxanes) of the general formula $[OSi_8O_{12}(OH)_2(EtO)_5]$, which cross-link with each other during spinning. The sol emerging from the (cold) die falls through the (warm) spin shaft where it undergoes a further (fourth) HCR which is responsible for the fact that the jet emerging from the die reacts via (molecular) cross-linking of the oligosilasesquioxanes to form a (stable) fiber. The length of the spin shaft is typically 1-5 m, advantageously 2 m. The climate in the spin shaft is temperature and humidity controlled and, if desired, it is also possible to set an atmosphere here of about 20° C. and about 35% (33-37%) atmospheric humidity with further reactants (ethyl nitrate for example).

After descending down the spin shaft, the fibers are round (not oval or even dumbbell-shaped) in cross section, do not have an undulating profile in longitudinal section, and are shape-stable. They are laid down on a traversing table. The mesh size of the fibrous nonwoven web thus formed is controlled via the traversing speed. The latter is of the order of a few cm/min. A slow forward advance thus creates a narrow-mesh fibrous nonwoven web wherein the TEOS as silicon-containing starting compound still retains more than 30% of its ethoxy groups.

The fibers produced according to the present invention in step (e1) exhibit a certain degree of hydro-phobicity, owing to the ethoxy groups still present. They are otherwise (very substantially) free of solvent (water, ethanol) and are best suitable for permanent storage, for transportation and distribution. In fact, one preferred embodiment of the present invention consists in producing the fibers, or fibrous nonwoven webs, to step (e1) of the powder, the monolith and the coated articles/surfaces to step (e2), (e3) and (e4) and to store, transport and distribute these embodiments of the present invention.

When step (a) utilizes dilute nitric acid, the possible and preferred reduction in acid strengthening step (e1), (e2), (e3) and (e4) is effected by the remaining, enclosed portion of the $NO_2$ (boiling point ~21.2° C.) then being removed by offgassing at preferably 30° C. When, however, the system utilizes an organic acid/arginine in place of nitric acid, the pH is raised, or the acid strength reduced, if desired, by means of, for example, Tris solutions (when the acid, and acetic acid is an example, cannot be driven off) shortly before application by rinsing in an aqueous Tris solution.

Self-evidently, storage and transportation in the case of (e4) are preferably effected in the "frozen" state of the PES material after step (c).

Step (e2)

Before or else during drying, the rPES material with a dynamic viscosity of about 60 Pa·s (shear rate 10 s$^{-1}$ at 4° C.), obtained from step (d) (which rPES material can be considered an active component by virtue of its bioactivity), can be admixed with any (further) active components, for example pharmaceutically active substances, or be covalently bonded thereto using a further, fourth HCR (hereinafter the term "active component", however, generally refers not to the rPES material from step (d) but to the further active component). This shall preferably be done by creating a homogeneous mixture. Particularly in the case of admixing temperature-sensitive active components, the mixture of PES material and active component(s) after the fourth HCR is subjected to gentle drying, for example spray or freeze drying. When the active component is not temperature-sensitive or no active component is added at all, drying can also be effected at (distinctly) elevated temperatures. In the process, it is preferable for a bioabsorbable and/or bioactive matrix to form around the active component. This matrix is also, in particular, suitable for encapsulating active components which are liquid (liquids can be enclosed in the matrix with long-term stability and be released again in a controlled manner). Encapsulation makes possible the mechanical and chemical stabilization of the active components, the improved handleability for such liquid active components and pharmaceuticals, and helps to prevent any uncontrolled volatilization of the active components. It will be appreciated that further substances and/or excipients appropriate to the particular use to be present in the final formulation (powder).

The powder can be a micropowder and/or a nanopowder. The particles of a micropowder according to the present invention have a size (an average diameter) which is preferably in the range from 0.01 µm to 100 µm and particularly in the range from 0.1 to 20 µm. The nanopowder particles generally have a size (an average diameter) of $\leq 100$ nm.

Step (e3)

In a further embodiment, the rPES material (dynamic viscosity at the end of (d) preferably not less than 70 Pa·s at a shear rate of 10 s$^{-1}$ at 4° C.) from step (d) (again before or during drying) can be admixed with a (further) active component, for example a pharmaceutically active substance, or be covalently bonded thereto by means of a fourth HCR. This is then followed, regardless of the presence of the (further) active component, by the casting of the rPES material into a shape. After drying, a monolith is obtainable in this way. Such monoliths can be used in the form of massive implants as drug delivery system subcutaneously, for example. They can be used for example as a depot for contraceptives and release the active component over a prolonged period. Such implants according to the present invention have good biological tolerability. The monoliths may preferably have a diameter of $\geq 0.5$ mm. Alternatively, the monoliths can also be comminuted and ground to powder.

Step (e4)

However, the ripened material from step (d) can also be processed into a coating. To this end, the article to be coated is coated by dipping into the rPES material (dynamic viscosity not less than 10 Pa·s; shear rate 10 s$^{-1}$ at 4° C.), by irrigation with the rPES material or by spin-coating or spraying the rPES material. Preference for use as coatings is given to those on coated tablets or capsules, for which pressed pulverulent pharmaceutical mixtures are provided with a bioabsorbable and/or bioactive coating of the rPES material. This allows the release of (further) active components within the formulation to be policed and/or controlled, for example via the layer thickness and/or the layer sequence. However, such a coating can also be applied to body-part implants (composed of titanium for example), which improves the (biological) tolerability of the implants; for example, rejection reactions are alleviated or prevented.

In a further embodiment of the present invention, high-viscosity sols, particularly hydrogels, can be supplemented or replaced by the rPES material of the present invention. High-viscosity sols and hydrogels are used in medicine and cosmetics as delivery systems for drugs or active components. Generally, hydrogels are widely used in the management of large-area wounds (wound treatment and wound healing). Advantageously, the addition of the rPES material makes it possible to improve the biological tolerability and hence wound healing. The hydrogels of the present invention can in this respect be advantageously used as bioabsorbable and/or bioactive products in medicine, particularly human medicine or medical technology.

Further Processing and Use of Fiber

The fibers as end products of one of the processes preferred according to the present invention (comprising the steps (a) to (d) and (e1)) can be used as fibers or else as fibrous nonwoven webs. These PES materials, like the PES and rPES material also, possess excellent bioabsorbability and/or bioactivity. These PES materials are also very useful for permanent storage, and for transportation and distribution.

Before use of the PES materials, preferably immediately before they are used, for example as bioabsorbable and/or bioactive materials in human medicine or medical technology (for example wound treatment, wound healing, as surgical suture or as reinforcing fibers; see also next paragraph below) the PES materials (fiber, powder, monolith, coating solution) are preferably watered and more preferably watered under slight external pressure. Watering serves to completely hydrolyze the remaining ethoxy groups still present and hence makes the materials more hydrophilic. As mentioned above, this watering can be effected under pH-elevating conditions (for example in a phosphate buffer $H_2PO_4^-/HPO_4^{2-}$), in particular when the raising of the pH has not already taken place in a preceding step. In the process, the fifth and last HCR proceeds, during which the nonhydrolyzed ethoxy groups still remaining are removed from the PES materials.

A further advantage is that the PES or rPES material produced according to the present invention, and the materials consisting thereof, have distinctly improved values in cytotoxicity tests compared with the fibers and fiber materials obtained by following the process of DE 196 09 551 C1. This improvement was evidenced in tests in the presence of L929 mouse fibroplasts. The materials obtained according to the present invention from steps (e1) to (e4) are therefore notable for particularly good biological tolerability.

The fibers or fibrous nonwoven webs produced according to the present invention can therefore be advantageously used as bioabsorbable and/or bioactive materials in human medicine, medical technology, filter technology, biotechnology or the insulant industry. More particularly, the materials produced according to the present invention can be used with advantage in the field of wound treatment and wound healing. Fibers can be used as surgical suture or as reinforcing fibers, for example. Fibrous nonwoven webs can be used with particular advantage in the management of surficial wounds, in the filtration of bodily fluids (blood for example) or in the field of bioreactors as a cultivation aid.

The present invention PES materials from (e1), (e2), (e3) and (e4), which can be loaded with a bioactive substance, i.e., which contain, in addition to the bioactive silicon polymer, a further active component, can transport these to the actual site of action, or influence the release of the active component at the site of action. These materials will hereinafter be referred to as drug delivery system.

The use of the ripened PES material according to the present invention and of the PES materials according to the present invention has the advantage that both can be processed, used and combined with various (further) active components in many different ways. It is particularly preferable when the rPES material of the present invention does not in the process form any reaction products with the (further) active component. The PES materials of the present invention are bioabsorbable and/or bioactive and exhibit improved cytotoxicity values, which contributes to improved biological tolerability of the materials, which is necessary in the fields of medicine and medical technology in particular.

The invention will now be more particularly described with reference to an example without it being restricted thereto.

All reported viscosities were measured with an MCR 300 viscometer from Physika at a shear rate of 10 s$^{-1}$ at 4° C.

EXAMPLE 1

Bioabsorbable and/or Bioactive rPES Material (sol) and its Processing into Fibers and Fibrous Nonwoven Webs By way of starting material for the hydrolysis condensation reaction, 2.7 mol of TEOS (tetraethoxysilane) (562.4 g) were introduced into a reaction vessel as initial charge. 3.4 (2.7× 1.26) mol of EtOH (156.8 g) were added as solvent. The mixture was stirred. Separately, 1N $HNO_3$ (27.81 g) was diluted with $H_2O$ (60.38 g). Subsequently, 89.28 g of this dilute nitric acid were added to the complete TEOS-EtOH mixture at RT, so that the resulting reaction mixture contains 1.8 mol of $H_2O$ and 0.01 mol of $HNO_3$ per mole of TEOS. The mixture was stirred for 5 hours.

The mixture obtained after step (a) was subsequently rendered almost water- and ethanol-free by evaporating in a rotary evaporator (step (b)) at 70° C. by applying a vacuum of 500 mbar and slow stirring (20 rpm). The high temperature served to substantially reduce the $HNO_3$ in the reduced form $NO_2$. The sol had a viscosity of about 1 Pa·s (shear rate of 10 s$^{-1}$ at 4° C.), there was a substantial decrease in acid strength.

The solution was cooled down to 4° C. in step (c) in a closed polypropylene beaker (ripening beaker) during 30 minutes and was subjected to ripening at 4° C. in step (d) for 8 days in the ripening beaker. A homogeneous single-phase sol dope having a viscosity of about 40 Pa·s (shear rate 10 s$^{-1}$ at 4° C.) was obtained. The sol had no discernible solid phase.

The sol was spinnable into fibers in step (e1). The sol is also referred to as spinning dope and as rPES material. The fibers were produced in a conventional spinning system. To this end, the spinning dope was filled into a cooled pressurized cylinder at −15° C., which was pressurized with an air pressure of 20 bar. The resulting force forced the spinning dope through dies. The emerging spinning dope (jet) had a diameter of 50 to 100 μm, depending on die diameter. The deliquescent, honey-like jet fell under its own weight into a spin shaft disposed underneath the pressurized cylinder and having a length of 2 m, where it reacted with the atmospheric humidity to form a shape-stable fiber which was round (not oval or even dumbbell-shaped) in cross section and had no undulating profile. The spin shaft was temperature and humidity controlled. The temperature was 20° C. and the atmospheric humidity was 35%. Shape-stable fibers were formed. The fibers were still slightly reactive at their surface. The postulated composition of the fibers is $[OSi_8O_{12}(OH)_2(EtO)_5]$ (oligosilasesquioxane). As they landed on the traversing table, the fibers adhered together at their areas of contact to form fibrous nonwoven webs. The fibrous nonwoven webs were subsequently aired at about 30° C. in a drying cabinet and the enclosed $NO_2$ further reduced. In the process, acid strength was reduced to a physiologically tolerable degree.

The fibrous nonwoven web produced in example 1 was subjected to a cytotoxicological test to ISO 10993-5 (1999); EN 30993-5 (1994). The cytotoxicity measured, compared with the values determined for the controls, revealed that the fibrous nonwoven web produced according to the present invention had no cytotoxic properties.

COMPARATIVE EXAMPLE

The reactants TEOS (tetraethoxysilane), EtOH, $H_2O$ and $HNO_3$ were mixed in a molar ratio of 1:1.26:X:0.01 (where X=1.6, 1.7, 1.8, 1.9 and 2.0) and vigorously stirred at room temperature for 5 hours. The resulting solutions were suspended in open vessels in a water bath temperature controlled to 70° C., where they remained until a defined weight loss had occurred. This was followed by cooling and filtration through a stainless-steel gauze having a mesh size of 1 mm×1 mm. The filtrate was exposed in a closed vessel to a ripening time of 6 hours to 6 months, depending on weight loss, at a temperature of 3° C. The resulting spinning dope was very homogeneous and lastingly stable and spinnable. The fibers were produced on a dry-spinning system. To this end, the spinning dope was filled into a spin head cooled to −15° C. and forced at a pressure of 10 to 15 bar initially through a stainless-steel gauze having a mesh size of 80×80 μm and then through a die having a diameter of 100 μm. The resulting continuous filament travelled across a drying sector of 1 m and was then wound up on a rotating cylinder. The cross-sectional shapes of the resulting fibers varied with the make-up batch, i.e., the amount of water added, between round, oval or dumbbell-shaped and had diameters between 5 μm and 30 μm. The cross-sectional areas were between 100 μm$^2$ to 400 μm$^2$.

The fiber surface is smooth and in no case exhibits an undulating profile. Tensile-strength measurements on the fibers revealed values from 100 MPa to 800 MPa.

IR spectra prepared from the fiber material show an Si—OH band at 950 cm$^{-1}$ and C—H signals at 3000 cm$^{-1}$. Thus there is a partially hydrolyzed and partially condensed ethoxy-silanol fibers after about 2 months' storage at room temperature, the IR spectrum no longer shows any C—H stretch bands. The fibers have converted into partially condensed silanol fibers which are stable for a period of several months.

The fibers thus produced were subjected to cytotoxicological measurements. The fiber material produced therefrom were subjected to the cytotoxicological test to ISO 10993-5 (1999); EN 30993-5 (1994) and found to have cytotoxic effects.

Moreover, only 50% of the entire reaction batch proved spinnable.

What is claimed is:

1. A polyethoxysiloxane (PES) material obtained by
   (a) performing a first hydrolysis-condensation reaction (HCR) of an X radical of one or more different silicon compounds of formula I $SiX_4$ (I), where the X radicals are the same or different and each represent hydroxyl, hydrogen or ethoxy, acid catalyzed, in the presence of water and in the presence of ethanol or of an ethanol-water mixture as solvent, for a period of 1 to 24 h at a temperature of 0° C. to 78° C.,
   (b) performing a second HCR of the material obtained in step (a) while at the same time removing the solvent by gradual evaporation in a gas diffusion tight container at a pressure of 100 to 1013 mbar, and a temperature of 50-78° C., until an increase in viscosity to 0.5-2 Pa·s, until weight constancy and until formation of a cyclotetrasiloxane of the formula $((SiO(OH)_{0.75} (OEt)_{1.25} \times 1/64 H_2O)_4$ and of molar mass of about 456 g;
   (c) cooling the polyethoxysiloxane material obtained in step (b) in a closed container over a period of from 2 to 5 minutes to 0.2 to 5 hours, to form a sol and, optionally;
   (d) converting the polyethoxysiloxane material obtained from (c) into an rPES material via a third HCR.

2. The material according to claim 1, wherein the pH of 0 to ≦7 in step (a) is set with dilute nitric acid or with an acidic mixture suitable for producing NO or $NO_2$ in situ or solution of (i) a physiologically tolerable acid and (ii) a substrate of nitroxide synthase (NOS).

3. The material according to claim 2, wherein the dilute nitric acid is used in a molar ratio of silicon compound(s) of formula (I) to nitric acid in the range from 90:1 to 110:1.

4. The material according to claim 1, wherein the acid strength is reduced in step (b), by evaporating $NO_2$ or by means of a Tris solution.

5. The polyethoxysiloxane material according to claim 1, wherein the polyethoxysiloxane material in step (c) is cooled down to −20° C. to +10° C.

6. The material according to claim 1, wherein the conversion of the polyethoxysiloxane to an rPES in step (d) is effected at a temperature of −20° C. to 10° C.

7. The material according to claim 1, wherein step (d) is performed until a viscosity of the material in the range from 30 to 55 Pa·s.

8. The material according to claim 1, wherein the silicon compound used in step (a) is tetraethoxysilane (TEOS).

9. Bioabsorbable or bioactive material comprising the polyethoxysiloxane material of claim 1.

10. Bioabsorbable or bioactive material according to claim 9, wherein said polyethoxysiloxane material is a fiber, a fibrous nonwoven web, powder, monolith or coating solution.

11. The Bioabsorbable or bioactive material according to claim 10, wherein the fiber, fibrous nonwoven web, powder, monolith or coating solution is watered immediately before use.

12. The material of claim 2, wherein said nitroxide synthase (NOS) is arginine.

13. The material of claim 2, wherein said physiologically tolerable acid is selected from the group consisting of citric, succinic, tartaric, acetic and ascorbic acids.

* * * * *